United States Patent
Hayakawa et al.

(10) Patent No.: US 8,134,697 B2
(45) Date of Patent: Mar. 13, 2012

(54) INSPECTION APPARATUS FOR INSPECTING PATTERNS OF SUBSTRATE

(75) Inventors: Koichi Hayakawa, Hitachinaka (JP); Masaaki Nojiri, Hitachinaka (JP)

(73) Assignee: Hitachi-High Technologies Corporation, Tokyo (JP)

( * ) Notice: Subject to any disclaimer, the term of this patent is extended or adjusted under 35 U.S.C. 154(b) by 466 days.

(21) Appl. No.: 12/366,217

(22) Filed: Feb. 5, 2009

(65) Prior Publication Data

US 2009/0208091 A1   Aug. 20, 2009

(30) Foreign Application Priority Data

Feb. 14, 2008   (JP) ................... 2008-032746

(51) Int. Cl.
  *G01B 11/26* (2006.01)
  *G01C 1/00* (2006.01)
(52) U.S. Cl. ................. 356/141.4; 356/154
(58) Field of Classification Search ........... 356/141–152
  See application file for complete search history.

(56) References Cited

U.S. PATENT DOCUMENTS

| | | | |
|---|---|---|---|
| 4,220,853 A * | 9/1980 | Feuerbaum et al. | 250/310 |
| 6,556,703 B1 * | 4/2003 | Kane et al. | 382/145 |
| 7,170,593 B2 * | 1/2007 | Honda et al. | 356/237.1 |
| 7,330,248 B2 * | 2/2008 | Sakai et al. | 356/237.4 |
| 7,518,383 B2 | 4/2009 | Gunji et al. | |
| 2005/0122508 A1 * | 6/2005 | Uto et al. | 356/237.2 |

FOREIGN PATENT DOCUMENTS

| | | |
|---|---|---|
| JP | 11-224336 | 8/1999 |
| JP | 2003-324135 | 11/2003 |
| JP | 2005-175333 | 6/2005 |
| JP | 2006-200944 | 8/2006 |
| JP | 2006-300848 | 11/2006 |

OTHER PUBLICATIONS

Miyoshi, G., "Feature: Looming Crisis of Wafer Inspection Technique Limit of Wafer Inspection Technique Pointed Out by Production Site II," Monthly Semiconductor World No. 8, 1995, pp. 96-99 (w/ partial English translation thereof).
Japanese Office Action issued in Japanese Patent Application No. 2008-032746, mailed Jun. 15, 2010.
English translation of Japanese Notification of Reasons for Refusal issued in Japanese Patent Application No. JP 2008-032746 dated Apr. 26, 2011.
Japanese Office Action issued in Japanese Patent Application No. 2008-032746, mailed Jun. 15, 2010.

* cited by examiner

*Primary Examiner* — Gregory J Toatley
*Assistant Examiner* — Jarreas C Underwood
(74) *Attorney, Agent, or Firm* — McDermott Will & Emery LLP (57) ABSTRACT

A degradation in throughput is prevented even in cases where it is necessary to reduce a pixel size during inspection according to a finer circuit pattern. In an inspection method and an inspection apparatus in which an inspected sample having a circuit pattern is irradiated with a charged particle beam to generate a signal, an image is obtained from the signal, and in which a defect of the circuit pattern is detected from the image, the inspection is performed while an inspected pixel size in a direction in which the charged particle beam is scanned relative to the inspected sample and an inspected pixel size in a stage moving direction are separately set. The stage is moved while the inspected sample is placed thereon.

6 Claims, 9 Drawing Sheets

| Inspection conditions | |
|---|---|
| Inspected pixel size | 50nm |
| Number of signal additions | 2 |
| Set | Cancel |

FIG. 4B

| Inspection conditions | |
|---|---|
| Inspected pixel size in scanning direction | 50nm |
| The number of pixels in scanning direction | 2048 |
| Inspected pixel size in stage direction | 70nm |
| Number of signal additions | 2 |
| Set | Cancel |

Stage moving direction

Scanning stripe

FIG. 5C  Scanning direction and stage moving direction : A nm Pixel

A nm PIXEL

A nm PIXEL (1)
(2)
(3)

Scanning direction
→ X
↓ Y
Stage moving direction

FIG. 6A

Scanning direction : A nm Pixel & Stage direction : B nm Pixel (A<B)

FIG. 6B

Scanning direction : B nm Pixel & Stage direction : A nm Pixel (A<B)

Schematic view of PLUG structure

FIG. 8B

Relationship between scanning time and signal amount

FIG. 9A
Inspection pixel size: B nm/The number of inspected pixels: C

FIG. 9B
Inspection pixel size: B×2 nm/The number of inspected pixels: C

FIG. 9C
Inspection pixel size: B×2 nm/The number of inspected pixels: C/2

FIG. 9D
Inspection pixel size: B×2 nm/The number of inspected pixels: C/2

INSPECTION APPARATUS FOR INSPECTING PATTERNS OF SUBSTRATE

BACKGROUND OF THE INVENTION

1. Field of the Invention

The present invention relates to a pattern inspection technique for an inspected sample having a fine circuit pattern, such as a semiconductor device and a liquid crystal display deice, particularly to method and apparatus for inspecting patterns on a wafer in the middle course of production of the semiconductor device.

2. Description of the Related Art

Examples of the inspected sample having the fine pattern include a semiconductor device, a substrate, a photomask (exposure mask), a liquid crystal display device and the like. Here, the inspection of the semiconductor wafer will be described by way of example. The semiconductor device is produced by repeating a process in which a pattern formed in a photomask is transferred onto a semiconductor wafer by lithographic treatment and etching treatment. In the semiconductor device production process, right or wrong of the lithographic treatment and etching treatment and generation of a foreign matter largely influence a yield of the semiconductor device. Accordingly, various apparatuses which inspect the pattern on the semiconductor wafer in the production process are used to early or previously detect the generation of the abnormality or defect.

For the apparatus which inspects the defect existing in the pattern on the semiconductor wafer, there is commercialized a defect inspection apparatus in which plural circuit patterns having the same shape formed on the wafer are irradiated with white light and the defect is inspected by comparing obtained optical images (for example, see Monthly Semiconductor World No. 8, 1995, pages 96 to 99). However, in the defect inspection apparatus, the defect whose size is smaller than the resolution of an optical system cannot be detected, and the defect is hardly detected in the finer and complicated circuit pattern.

Therefore, in order to inspect the circuit pattern using an electron image having a resolution higher than that of the optical image, there is proposed a method or an apparatus, wherein a secondary electron or a reflection electron generated by irradiating the semiconductor wafer with a charged particle beam such as the electron beam is detected, and the defect is detected with the use of an electron beam image based on the detected signal of the secondary electron or reflection electron. However, when the charged particle beam is used, a charging phenomenon may occur depending on the structure or material of the semiconductor wafer pattern. Unfortunately the charging phenomenon lowers image contrast or defect detection performance. Recently, because the structure or material is getting diversified with finer semiconductor wafer pattern, the defect detection performance heavily depends on a charged state of the semiconductor wafer. Therefore, the charged state of the semiconductor wafer is changed or controlled by changing or controlling energy, a current amount, the number of irradiation times of the charged particle beam or by changing or controlling capturing timing of a secondary electron signal generated from the semiconductor wafer (for example, see Japanese Patent Application Laid-Open (JP-A) No. 2005-175333).

In order to enhance defect inspection accuracy to deal with finer circuit pattern, a pixel size is reduced to improve the image resolution during the inspection. There is also disclosed a technique, wherein the pixel size is reduced only in a portion suspected to be a defect, and the inspection accuracy is improved without lengthening the inspection time (for example, see JP-A No. 2006-200944).

However, when the pixel size is simply reduced with the finer circuit pattern during the inspection, the throughput is largely degraded. For example, currently the same value of the inspected pixel size is adopted in a direction in which the charged particle beam is scanned and a direction in which the stage is moved. When the pixel size becomes a half, the inspection throughput is degraded to a quarter. When the pixel size is reduced only in the portion suspected to be the defect as described above, a process for searching the portion suspected to be the defect is required, which results in the increased inspection time.

SUMMARY OF THE INVENTION

In view of the problem, an object of the invention is to provide an inspection method and an inspection apparatus, wherein the degradation in inspection throughput is prevented by reducing the pixel size only for the direction in which high resolution is required, that is, the pixel size in the scanning direction and the pixel size in the stage moving direction are separately set according to the structure or material of the wafer.

In order to solve the problem, in the invention, an inspected pixel size (signal detection interval) in the direction (X-direction) in which the charged particle beam is scanned relative to the inspected sample and an inspected pixel size in the stage moving direction (Y-direction) are separately set, the pixel size is reduced to prevent an oversight of the defect in the direction in which the detection accuracy is required, and the pixel size is enlarged to prevent the degradation in throughput in the direction in which the detection accuracy is not so much required.

Namely, a circuit pattern inspection apparatus in the invention includes irradiation means for irradiating an inspected sample with a charged particle beam, a circuit pattern being formed in the inspected sample; scanning means for scanning the charged particle beam in an X-direction at an arbitrary speed; stage moving means for moving the inspected sample in a Y-direction at an arbitrary speed while the inspected sample is placed thereon, the Y-direction being different from the X-direction; detection means for detecting a signal, the signal being generated from the inspected sample by the irradiation with the charged particle beam; memory means for imaging the signal detected by the detection means and storing the image therein; comparison means for comparing the image stored in the memory means to an image obtained from another circuit pattern corresponding to the circuit pattern; and determination means for determining a defect on the circuit pattern from the comparison result performed by the comparison means. In the configuration, the scanning speed in the X-direction and the moving speed in the Y-direction may be separately controlled, so that the scanning speed and the moving speed can be adjusted at proper speeds according to the structure or material of the circuit pattern. Therefore, in such cases where the fine defect is generated in a particular direction as the wiring pattern, the degradation in throughput can be prevented without lowering the defect detection accuracy.

In accordance with an another aspect of the invention, a circuit pattern inspection apparatus includes irradiation means for irradiating an inspected sample with a charged particle beam, a circuit pattern being formed in the inspected sample; scanning means for scanning the charged particle beam in an X-direction; stage moving means for moving the inspected sample in a Y-direction while the inspected sample is placed thereon, the Y-direction being different from the X-direction; detection means for detecting a signal, the signal being generated from the inspected sample by the irradiation with the charged particle beam; memory means for imaging the signal detected by the detection means and storing the image therein; comparison means for comparing the image stored in the memory means to an image obtained from another circuit pattern corresponding to the circuit pattern; determination means for determining a defect on the circuit pattern from the comparison result performed by the comparison means; and setting means for setting each of a pixel size in the X-direction and a pixel size in the Y-direction to an arbitrary pixel size, the pixel size in the X-direction being inspected by the scanning of the scanning means, the pixel size in the Y-direction being inspected by the movement of the stage moving means. Thus, the different pixel sizes are set in the X-direction and Y-direction, so that the degradation in throughput can be prevented without lowering the defect detection accuracy while the pixel size is properly adjusted according to the structure or material of the circuit pattern.

In the circuit pattern inspection apparatus according to an another aspect of the invention, the setting means may include means for setting the number of pixels in the X-direction inspected by the scanning of the scanning means. Therefore, the defect detection sensitivity can be improved, and the degradation in throughput can be prevented by setting the number of pixels to a proper value.

In accordance with an another aspect of the invention, a circuit pattern inspection method in which an inspected sample in which a circuit pattern is formed is irradiated with a charged particle beam to generate a signal from the inspected sample, an image is obtained by imaging the signal, the image is compared with an image obtained from another circuit pattern corresponding to the circuit pattern, and a determination of a defect on the circuit pattern is made based on the comparison result, wherein inspection is performed while a pixel size in an X-direction and a pixel size in a Y-direction are separately set, the pixel in the X-direction being inspected by scanning the charged particle beam in the X-direction of the inspected sample, the pixel size in the Y-direction being inspected by moving the inspected sample in the Y-direction which is different from the X-direction. Further, in this case, the circuit pattern inspection method according to the invention may include performing inspection by setting each of the pixel size in the X-direction and the pixel size in the Y-direction to an arbitrary pixel size according to a structure of the circuit pattern or the structure and a material of the circuit pattern. Preferably the circuit pattern inspection method according to the third aspect of the invention includes performing inspection by setting the number of pixels in the X-direction. Therefore, the pixel size in the X-direction and the pixel size in the Y-direction can properly be adjusted according to the structure or material of the circuit pattern, and the degradation in throughput can be prevented without lowering the defect detection accuracy.

DESCRIPTION OF THE PREFERRD EMBODIMENT

An embodiment of the invention will be described below with reference to the drawings.

Figure 1:
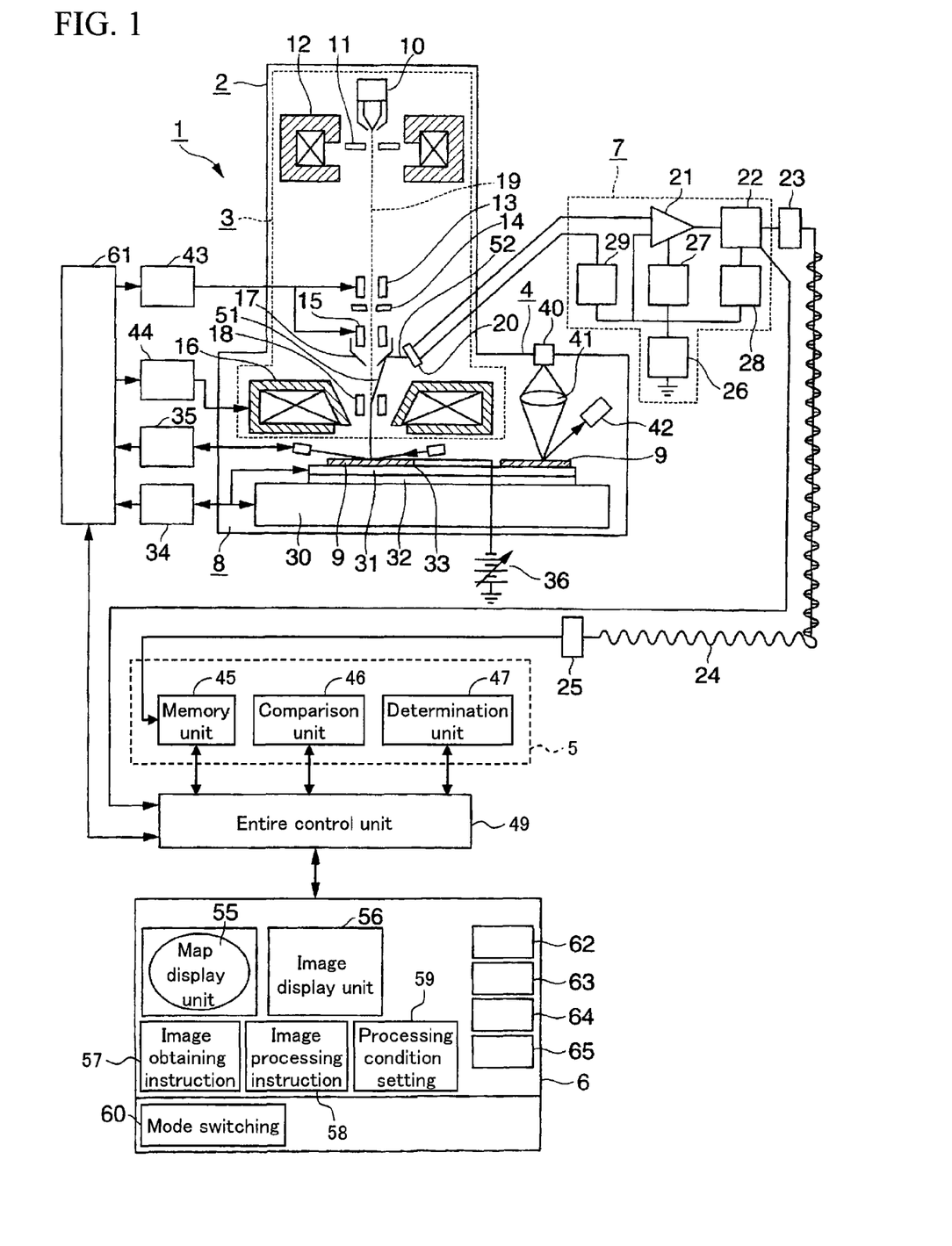
FIG. 1 is a schematic diagram showing a configuration of a circuit pattern inspection apparatus according to the invention.

FIG. 1 is a schematic diagram showing a configuration example of a circuit pattern inspection apparatus 1 according to the invention. The circuit pattern inspection apparatus 1 includes an inspection chamber 2 which can be evacuated by a pump (not shown), an image processor 5 which processes sent image data, an entire control unit 49 which controls an operation of each unit, an input unit 6 by which an operation command of each unit or an inspection condition is fed, and a secondary electron detecting unit 7 which detects, amplifies, and converts a signal.

The inspection chamber 2 mainly includes an electron optical system 3, an optical microscope unit 4, and a sample chamber 8. The inspection chamber 2 also includes a spare chamber (not shown in the embodiment) in which an inspected sample 9 is conveyed. The spare chamber can be evacuated independently of the inspection chamber 2.

The electron optical system 3 includes an electron gun 10 which generates an electron beam, an electron beam extracting electrode 11, a condenser lens 12 which condenses the electron beam, a blanking deflector 13, a scanning deflector 15, a aperture 14, an objective lens 16, a beam reflector 17, and an ExB deflector 18. The blanking deflector 13 and the scanning deflector 15 are connected to a scanning signal generator 43. The blanking deflector 13 and the scanning deflector 15 can control deflection of the electron beam based upon a blanking signal and a scanning signal which are supplied from the scanning signal generator 43, respectively. The condenser lens 12 and the objective lens 16 are connected to a lens power supply 44. In each of the condenser lens 12 and the objective lens 16, a aperture amount of the electron beam can be adjusted by a signal supplied from the lens power supply 44.

The optical microscope unit 4 includes a light source 40, an optical lens 41, and a CCD camera 42. The optical microscope unit 4 is disposed near the electron optical system 3 in the inspection chamber 2, and the optical microscope unit 4 is disposed at a position to such an extent distant from the electron optical system 3 that the electron optical system 3 and the optical microscope unit 4 do not influence each other. A distance between the electron optical system 3 and the optical microscope unit 4 is already known, and the inspected sample 9 can be reciprocated between the electron optical system 3 and the optical microscope unit 4 by an X-stage 31 or a Y-stage 32. Therefore, the inspected sample 9 is disposed in an optical axis of the electron optical system 3 when an electron microscopic image is observed, and the inspected sample 9 is disposed in an optical axis of the optical microscope unit 4 when an optical microscopic image is observed.

The sample chamber 8 includes a sample stage 30, the X-stage 31, the Y-stage 32, a rotary stage 33, a position measuring and position controlling device 34, and an inspected sample height measuring device 35. The inspected sample 9 placed on the sample stage 30 can be moved in an X-direction and a Y-direction by the X-stage 31 and the Y-stage 32, respectively, and the inspected sample 9 can be rotated about a Z-axis (direction perpendicular to the XY plane) by the rotary stage 33.

The secondary electron detecting unit 7 includes a secondary electron detector 20 which detects a secondary electron 51 generated from the inspected sample 9, a preamplifier 21 which amplifies a signal, an AD converter 22, light conversion means 23, light transmission means 24 such as an optical fiber, electric conversion means 25, a high-voltage power supply 26, a preamplifier driving power supply 27, an AD converter driving power supply 28, and a reverse bias power supply 29. The secondary electron detector 20 is provided in the inspection chamber 2, and the secondary electron detector 20 is disposed above the objective lens 16. The secondary electron detector 20, the preamplifier 21, the AD converter 22, the light conversion means 23, the preamplifier driving power supply 27, and the AD converter driving power supply 28 are floated at a positive potential by the high-voltage power supply 26. The secondary electron 51 generated from the inspected sample 9 is guided to the secondary electron detector 20 by an attractive electric field created by the positive potential.

The image processor 5 includes a memory unit 45, a comparison unit 46, and a determination unit 47. An image signal sent through light transmission means 24 is stored in the memory unit 45. The comparison unit 46 compares at least two images stored in the memory unit 45. The determination unit 47 determines a defect from the image comparison result performed by the comparison unit 46.

The input unit 6 includes a map display unit 55, an image display unit 56, and various command units. The map display unit 55 performs mapping display of defect position on the inspected sample based on the result of the image processor 5. The image display unit 56 displays an electron beam image based on the signal captured by the secondary electron detecting unit 7, and displays an optical image through the electron microscope 4. The various command units by which a user sets and indicates an operation condition and inspection condition of each unit of the apparatus include commands 62 to 65 used for inspection start, end, save, and the like, an image obtaining instruction 57, an image processing instruction 58, a processing condition setting 59, a mode switching 60, etc.

The electron beam (hereinafter referred to as primary electron beam 19) with which the inspected sample 9 is irradiated is extracted from the electron gun 10 by applying a voltage between the electron gun 10 and the electron beam extracting electrode 11. The primary electron beam 19 can be accelerated by applying a high-voltage negative potential to the electron gun 10. Therefore, the primary electron beam 19 travels in the direction of the sample stage 30 by energy corresponding to the potential, and is focused by the condenser lens 12, narrowed down by the objective lens 16, and applied to the inspected sample 9 (a substrate, such as a semiconductor wafer or chip, a liquid crystal display panel, and a mask, which has a fine circuit pattern) mounted on the X-Y-stages 31 and 32 on the sample stage 30. The primary electron beam 19 is controlled by the scanning deflector 15 so as to scan the inspected sample 9. A retarding power supply 36 can apply a negative voltage to the inspected sample 9. The primary electron beam can be decelerated by adjusting the voltage of the retarding power supply 36, and the electron beam irradiation energy to the inspected sample 9 can be adjusted to an optimum value without changing the potential at the electron gun 10.

The secondary electron 51 which is generated by irradiating the inspected sample 9 with the primary electron beam 19 is accelerated by the negative voltage applied to the inspected sample 9. The ExB deflector 18 is disposed above the inspected sample 9, and the accelerated secondary electron 51 is deflected toward a predetermined direction by the ExB deflector 18. The ExB deflector 18 can change a deflection amount of the secondary electron 51 by adjusting intensities of an electric field and a magnetic field which are applied to the secondary electron 51. The electric and magnetic fields can be varied with the negative voltage applied to the inspected sample 9. The secondary electron 51 deflected by the ExB deflector 18 collides with the beam reflector 17 under predetermined conditions. The beam reflector 17 is formed into a conical shape, and the beam reflector 17 has a shield-pipe function of shielding against the electron beam 19 with which the inspected sample 9 is irradiated. When the accelerated secondary electron 51 collides with the beam reflector 17, a second secondary electron 52 having energy of several to 50 electron volts is generated from the beam reflector 17.

The generated second secondary electron 52 is guided to the secondary electron detector 20. At this point, the secondary electron detector 20 detects the second secondary electron 52 in synchronization with scanning timing of the primary electron beam 19. An output signal detected by the secondary electron detector 20 is amplified by the preamplifier 21 disposed outside the inspection chamber 2, and converted into digital data by the AD converter 22. The digital data is sent by the light transmission means 24 such as the optical fiber, from the light conversion means 23 to the image processor 5 through the electric conversion means 25. At this point, because the detected output signal is sent after being converted into digital data, the signal can be sent to the image processor 5 at higher speed and with higher SN ratio as compared with the conventional technique.

While the signal (image signal) sent to the image processor 5 is stored in the memory unit 45, the signal is sent to the input unit 6 to be image-displayed on the image display unit 56. The comparison unit 46 performs comparison operation of the stored image signal and an image signal which is obtained from another same pattern located away from the inspected sample by a predetermined distance. That is, alignment between the images, normalization of a signal level, and various pieces of image processing for removing a noise signal are performed to perform the comparison operation. Then the determination unit 47 compares a predetermined threshold to an absolute value of a resultant difference image signal from the comparison operation. When the absolute value of the difference image signal is larger than the predetermined threshold, the determination unit 47 determines that the corresponding pixel is a defect candidate, and the determination unit 47 sends the result to the input unit 6 through the entire control unit 49. In the input unit 6, the defect position and the number of defects are displayed on the map display unit 55.

The operation command and operation condition of each unit of the apparatus are fed from the input unit 6. In the input unit 6, conditions such as an acceleration voltage in generating the electron beam, an electron beam deflection width, a deflecting speed, signal capturing timing of the secondary electron detecting device, and a sample stage moving speed are inputted in advance so that they can be set arbitrarily or selectively in accordance with the purpose of inspection. Under the conditions set by the input unit 6, the entire control unit 49 monitors a shift of a position or a height through a correction control circuit 61 based on the signals supplied from the position measuring and position controlling device 34 and height measuring device 35, and the entire control unit 49 supplies a correction signal to the correction control circuit 61 depending on the result. The correction control circuit 61 controls the scanning deflector 15 and the objective lens power supply 16 using the scanning signal generator 43 and the lens power supply 44 based on the correction signal, and the correction control circuit 61 adjust the electron beam such that a correct position of the inspected sample 9 is always irradiated with the electron beam. In cases where blanking of the primary electron beam 19 is required, an instruction of the blanking is provided through the input unit 6, the entire control unit 49 makes the scanning signal generator 43 supply a blanking signal to the blanking deflector 13 through the correction control circuit 61. Therefore, the primary electron beam 19 is deflected, and the electron beam is controlled so as not to pass through the aperture 14.

In the embodiment, a length measuring unit in which laser interference is utilized is used for measuring the position in the position measuring and position controlling device 34. The positions of the X-stage 31 and Y-stage 32 are monitored in real time by the position measuring and position controlling device 34, and the positional information is transferred to the input unit 6. Pieces of data such as motor revolving speeds of the X-stage 31, Y-stage 32, and rotary stage 33 are also transferred from their respective drivers to the input unit 6. The input unit 6 can correctly recognize the region and position irradiated with the primary electron beam 19 based on the pieces of data, and the shift of the position irradiated with the primary electron beam 19 can be corrected in real time by the correction control circuit 61 if needed.

An optical measuring device which is of a non-electron-beam measuring system, for example, a laser interferometer or a reflection optical measuring device which measures a change in position by reflected light is used as the height measuring device 35. The height measuring device 35 can measure the height of the inspected sample 9 mounted on the X-Y-stages 31 and 32 in real time. In the embodiment, the inspected sample 9 is irradiated with elongated white light having passed through a slit, through a transparent window, the position of the reflected light is detected by a position detection monitor, and a height change amount is computed from the position fluctuations. A focal distance of the objective lens 16 is dynamically corrected to finely narrow down the primary electron beam 19 based on the measurement data of the height measuring device 35, so that the inspected region can be irradiated with the primary electron beam 19 which is always in focus thereon. A warp, height, and distortion of the inspected sample 9 are measured in advance before the inspected sample 9 being irradiated with the electron beam, and correction condition of the objective lens 16 may be set for each inspection region by the input unit 6 based on the measured warp, height, and distortion data.

In the invention, with reference to a method for controlling the position where the inspected sample 9 is irradiated with the primary electron beam 19, a scanning position in the X-direction is controlled by controlling the deflection of the primary electron beam 19 in the X-direction, and the position in the Y-direction by controlling the movement of the Y-stage 32 in the Y-direction. Specifically the entire control unit 49 supplies a control signal based on the conditions, such as pixel size and the number of pixels, which are set by the input unit 6, and the scanning signal generator 43 supplies a scanning signal to the scanning deflector 15 in response to the control signal. In the scanning deflector 15, a deflection amount in the X-direction of the primary electron beam 19, that is, a scanning position in the X-direction is controlled based on the supplied scanning signal (by increasing or decreasing a deflection voltage Vx in the X-direction of the scanning deflector 15 while a deflection voltage Vy in the Y-direction being controlled to be constant). Similarly, based on the control signal supplied from the entire control unit 49, the position measuring and position controlling device 34 controls the movements in the Y-directions of the X-Y-stages 31 and 32, thereby controlling the position in the Y-direction where the inspected sample 9 is irradiated with the primary electron beam 19. In the invention, the scanning position in the X-direction and the stage movement in the Y-direction can be separately controlled. That is, the pixel size and the number of pixels in the X-direction and the pixel size and the number of pixels in the Y-direction can be set to their respective arbitrary values.

The method for controlling the position where the inspected sample 9 is irradiated with the primary electron beam 19 is not limited to the above method. For example, a method in which the primary electron beam 19 is two-dimensionally (X-direction and Y-direction) scanned while the X-Y-stage 31 and 32 on which the inspected sample 9 is placed is immobilized during execution of inspection or a method in which the primary electron beam 19 is scanned in the X-direction while X-Y-stages 31 and 32 are continuously moved in the Y-direction at a constant speed during execution of inspection can be adopted. The former effectively inspects a certain relatively-narrow region, and the latter effectively scans a relatively-broad region.

In the inspection apparatus and inspection method of the invention, it is necessary to increase an inspection speed. Accordingly, in the embodiment, unlike usual SEM (Scanning Electron Microscopy), the electron beam having an electron beam current of pA order is neither scanned at a low speed, nor the electron beam is scanned many times to overlap the images. In order to prevent the charging of an insulating material, it is necessary to scan the electron beam one time or several times at a high speed. In the embodiment, the image is formed by scanning the electron beam having a large current of 100 nA only once. The current of 100 nA is about 100 or more times as large as that of the usual SEM. A scanning width is set to 100 μm, one pixel has a size of 0.1 square μm, and one-time scanning is performed for 1 μs.

In the embodiment, preferably a diffusion refill type thermal field emission electron source is used as the electron gun 10. The use of the electron gun 10 can ensure the stable electron beam current as compared with a conventional tungsten filament electron source and cold field emission electron source, thereby obtaining an electron beam image with a small variation in brightness. Since the electron beam current can largely be set by means of the electron gun 10, high-speed inspection can be achieved.

Figure 2:
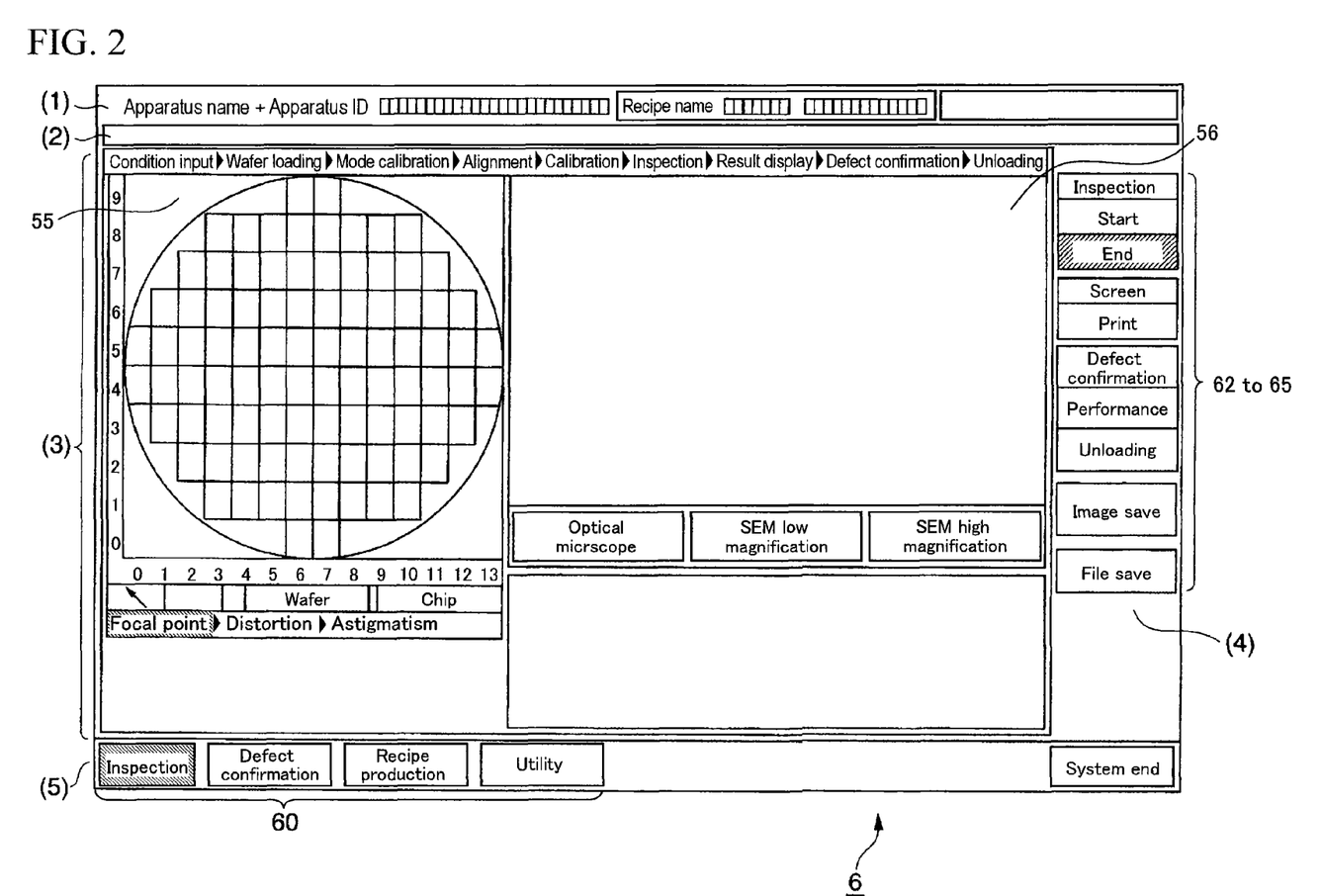
FIG. 2 is a screen view showing a configuration of an input unit of the invention.

FIG. 2 is a screen view showing a configuration of the input unit 6 (GUI (Graphical User Interface)) of the invention. In the embodiment, the input unit 6 is roughly divided into five regions. A region (1) is disposed in an upper portion of the screen, and an apparatus name, apparatus ID, and category file name and a process file name which are of a recipe name are displayed in the region (1). Guidance for explaining a manual operation and a state is displayed in a region (2). A user can smoothly advance the manual operation by confirming the guidance. The map display unit 55 and the image display unit 56 are included in a region (3) in the center of the screen, display contents are changed according to the manual operation or the state of progress. Manual operation buttons which are commonly necessary in plural screens are displayed in a region (4) on the right of the screen. Examples of the manual operation buttons include "print", "file save", "start", "end", "image save" and the like (corresponding to commands 62 to 65 of FIG. 1). For example, when "file save" is pressed, a screen for specifying the names of the category file and process file to store the currently producing recipe is displayed, and the recipe is stored with the file names specified in the screen. When "image save" is pressed, a screen for specifying a name for storing the currently displayed image as an image file is displayed, and the image is stored with the name specified in the screen. Mode names (corresponding to mode switching 60 of FIG. 1) such as "inspection", "defect confirmation", "recipe production", and "utility" are displayed in a manual operation region (5) in a lower portion of the screen. For example, when "inspection" is pressed, the apparatus enters a mode in which an automatic inspection is performed, and when "recipe production" is pressed, the apparatus enters a recipe producing mode in which an inspection parameter is set. Thus, the user can perform the setting of the inspection condition with good visibility and operability using GUI in which graphics are used to display pieces of information. The configuration of the input unit 6 is shown in FIG. 2 only by way of example, and various interfaces changed and modified in many ways can be applied to the invention.

Figure 3:
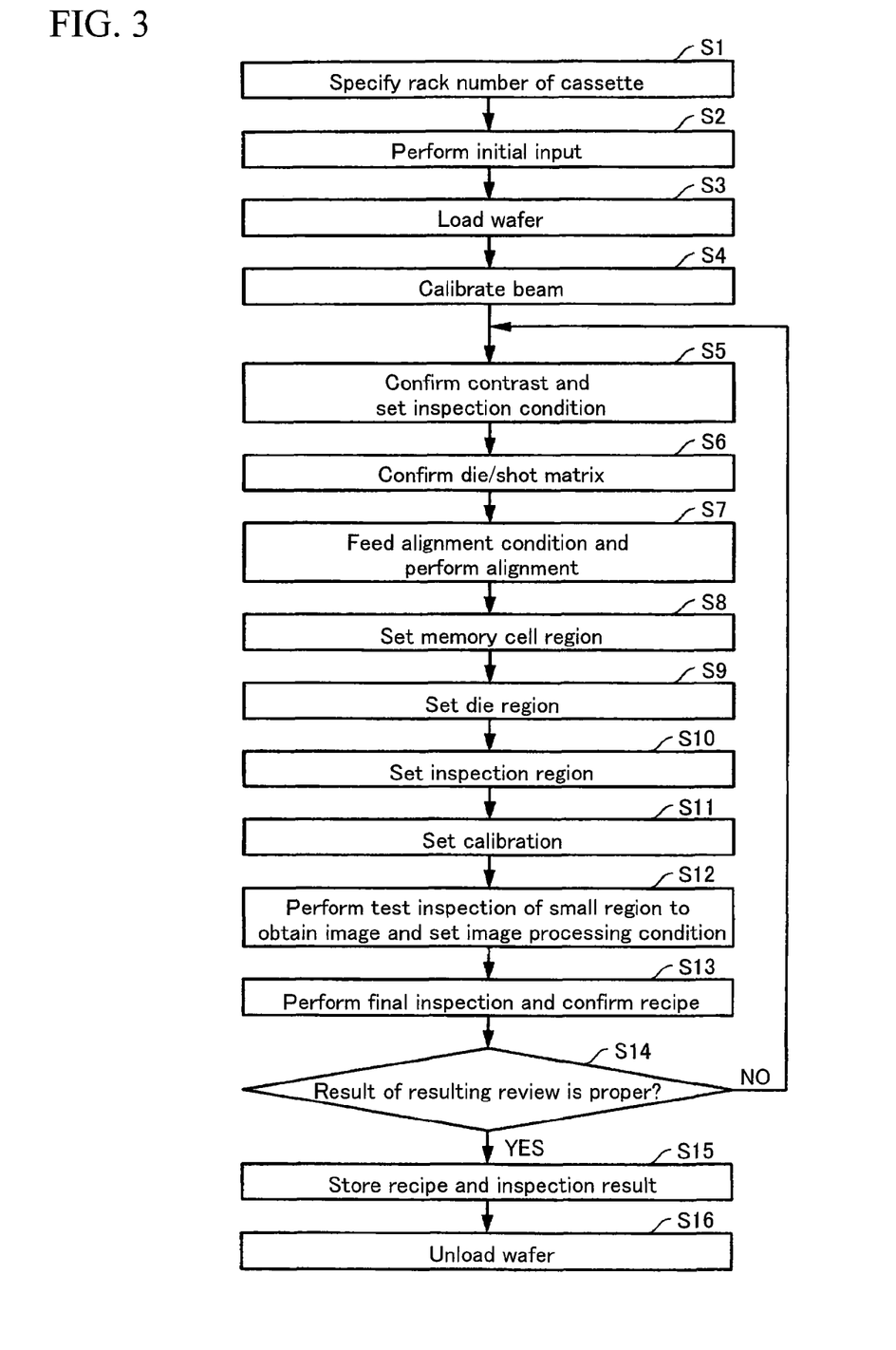
FIG. 3 is a flowchart showing a recipe producing procedure.

A recipe producing method in the recipe producing mode will be described with reference to FIG. 3. FIG. 3 is a flowchart showing a recipe producing procedure in the recipe producing mode. As described above, in the GUI screen of FIG. 2, when the "recipe production" mode of the region (5) is selected, the GUI screen is switched to a recipe producing screen of FIG. 3. In the recipe producing screen of FIG. 3, a start button is pressed to specify a rack number (S1). A recipe file is called to perform an initial input such as new or change input, lot ID, and wafer ID (S2). A wafer cassette is placed on a loader of the inspection apparatus (S3). Processing items of the loader includes (1) OF (Orientation Flat) or a notch is detected, (2) the wafer is retained in the sample holder (sample exchange chamber), and (3) the sample holder is moved to an inspection chamber stage. Then the sample is moved to a stage reference mark to perform absolute calibration of the beam (S4). At this point, the calibration is performed based on a default recipe file condition, (1) the sample is irradiated with the beam, (2) deflection correction and reference coordinate correction are performed, and (3) a focal point parameter is corrected.

Figure 4A:
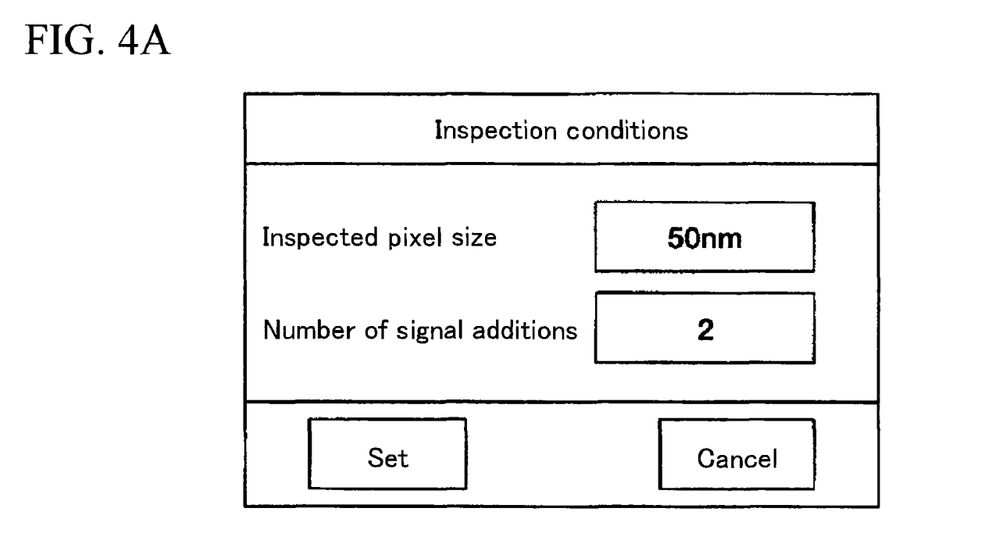
FIGS. 4A and 4B show an inspection condition setting screens.
Figure 4B:
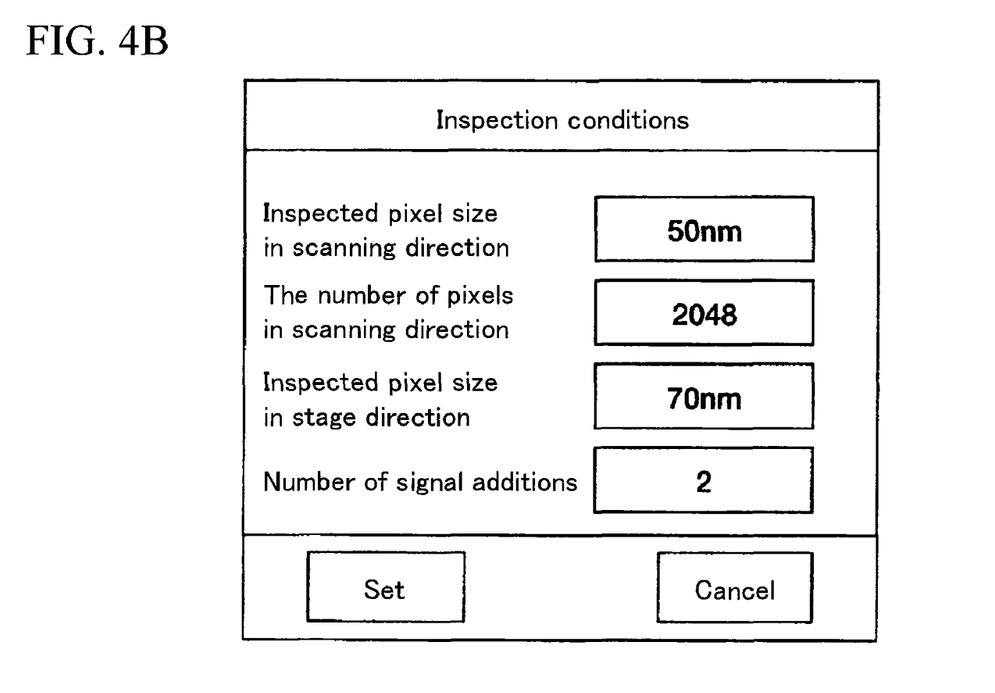

The position specified on the sample is irradiated with the electron beam to confirm the image contrast on the sample, and the focal point and astigmatism are adjusted again (S5). At this point, the inspection conditions (such as the electron beam acceleration voltage, the electron beam current, the number of signal additions in reading the signal, the pixel size, and the number of pixels) are changed unless the sufficient contrast is obtained. FIGS. 4A and 4B show an example of the screen on which the inspection conditions are set, FIG. 4A shows a conventional setting screen, and FIG. 4B shows a setting screen of the invention. In the conventional setting screen (FIG. 4A), because the same pixel size is employed in the scanning direction (X-direction) and stage moving direction (Y-direction), only one input unit exists as an inspected pixel size. On the other hand, in the setting screen of the invention (FIG. 4B), the inspected pixel sizes can separately be set in the scanning direction and stage moving direction. In the invention, as shown in FIG. 4B, the number of pixels in the scanning direction can be set in order for an inspection width in the scanning direction to be specified. Therefore, the inspection can be performed with different pixel sizes in the X-direction and Y-direction. For example, in cases where the inspection is performed for the circuit pattern such as a wiring pattern in which a defect structure has different sizes and complexity in the X-direction and Y-direction, the degradation in throughput can be prevented to perform the inspection. The number of pixels can be set, the improvement of the defect detection sensitivity can be achieved, and the degradation in throughput can be prevented by appropriately setting the inspection width.

When the electron beam irradiation condition is determined to confirm the contrast, a shot size of the wafer and a size and arrangement of die (chip) are fed (S6). Specifically, the shot size and a shot matrix are fed, and the arrangement of dies in the shot is fed. Then the presence or absence of shots or dies in a wafer peripheral portion are specified.

An alignment condition input and alignment are performed (S7). Specifically, (1) alignment chips are specified (plural pieces), (2) movement to an origin of a first chip, (3) an optical microscope monitor is switched to, and (4) manual movement to an alignment mark position of the first chip, (5) an optical image is registered, (6) the apparatus is switched to a SEM image mode, (7) the beam is manually finely adjusted to alignment mark position, (8) a SEM image is registered, and (9) an alignment coordinate is registered. Alignment performing items include (1) movement to the first point, (2) image input, searching, and matching, (3) movement to the second point, (4) image input, searching, and matching, (5) movement to the remaining point, searching, and matching, and (6) inclination, position and chip interval corrections. A chip origin offset setting includes (1) movement to a final point alignment mark, (2) a position of an alignment mark is specified (SEM image mode), (3) movement to the origin of first point, (4) a position of the chip origin is specified (SEM image mode), and (5) an offset between the chip origin and the alignment mark is calculated and registered. The offset of the chip origin shall mean a distance between the alignment coordinate and the origin coordinate of the chip in which the alignment mark exists.

A memory cell region is set in the chip (S8). The memory cell region is a unit of the size of the image stored in the memory unit 45 of FIG. 1, and the comparison unit 46 performs the comparison inspection in units of cell. Accordingly, it is necessary that a circuit pattern in a certain cell corresponds to circuit patterns in other cells. The specific setting method includes (1) the cell region is fed, (2) a cell pitch is fed, and (3) the cell region and the cell pitch are registered. The input of the cell region is performed using the optical microscopic image and the electron beam image. A die region setting is performed, that is, an inspection region and a non-inspection region in the die region are set (S9). Specifically, (1) the die region is fed, (2) the die inspection region is fed, and (3) the die region and the die inspection region are registered. The die region input is also performed using the optical microscopic image and the electron beam image. An inspection region is specified (S10). At this point, a die which is of inspection target among the dies on the wafer map is specified, the inspection region in the die is specified, an inspection sampling rate to the specified region is specified, and an image obtaining direction is specified.

When the specification of the inspection region is completed, the mode is transferred to a calibration setting in which brightness during inspection is adjusted (S11). In the calibration, the image is obtained and gain adjustment or brightness correction of hardware is performed according to the signal amount on the basis of a brightness distribution in the image. Actually the calibration is performed while the die to which the calibration is performed and the coordinate in the die are specified.

The image is actually obtained under already set conditions, and image processing conditions for detecting the defect are set (S12). A kind of a filter used for the detection signal when obtaining the image is selected. The image of a small region in one chip is obtained under the same conditions as the actual inspection. As used herein, the small region shall mean a region having a width of 100 µm and a length of one chip. The width of 100 µm corresponds to the scanning width of the electron beam. When the image is obtained, a threshold for defining the defect is fed. When the determination of the defect is made, the image of the defect point is displayed. The operation is repeated to obtain the optimum inspection conditions. The series of operations is referred to as "small region test inspection".

Thus, various parameters necessary for the inspection can be set by the above various inputs. However, in the case of actual semiconductor wafer, the image processing condition setting for the small region test inspection is not enough because a variation in process exists in the wafer surface or among production lots, and it is necessary to determine the threshold for the defect definition in consideration of the variations. Therefore, final inspection is performed using the produced recipe file (S13). That is, (1) stage constant speed continuous movement, the position, and the height are monitored, (2) the beam scanning and real-time correction (stage and Z-sensor following) are performed, (3) the secondary electron is detected, the AD conversion is performed, and the image is fed into the image memory, (4) the image processing and comparison determination are performed, (5) the beam is corrected every N stripes, and (6) the number of defects and defect positions are displayed. A defect detection level or a false detection level is confirmed based on the monitoring result, to determine whether or not the inspection conditions are proper (S14). When the inspection conditions are proper, various fed parameters are registered (S15). Finally the wafer is unloaded (S16). On the other hand when the inspection conditions are not proper, the process returns to step S5 to set the inspection conditions again.

In the recipe producing mode, all the items are newly set. However, only the necessary portion may be set while the already produced recipe is used (update form), or some of the items may automatically be set. The pixel sizes in the X-direction and Y-direction and the number of pixels are not set in the recipe producing mode, but they may be set from the input unit which is provided in the form of a pull-down menu on the GUI screen.

The scanning means for scanning the charged particle beam, the stage moving means, and the signal detection of the invention will be described below.

Figure 5A:
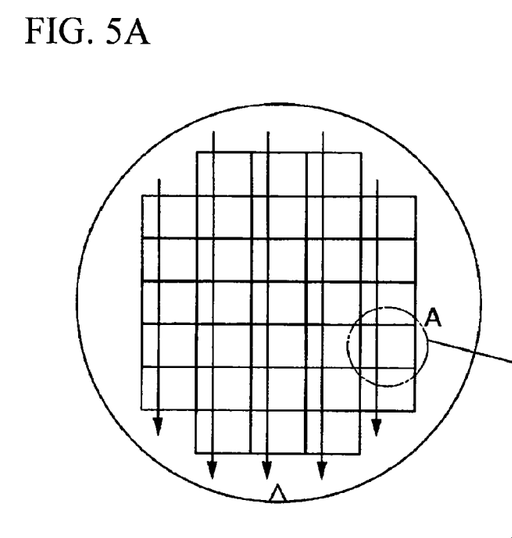
FIGS. 5A, 5B and 5C are views explaining irradiation means for irradiating an inspection wafer with a charged particle beam and a signal detection position.
Figure 5B:
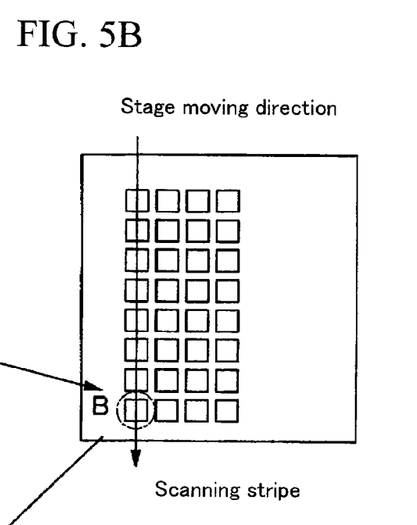
Figure 5C:
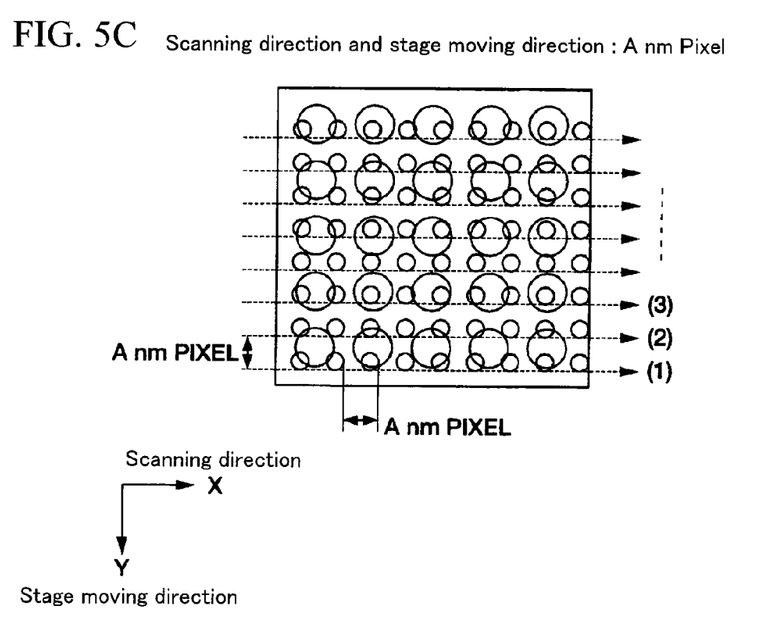

FIGS. 5A-5C show the scanning direction of the charged particle beam (primary electron beam 19), the moving direction of the stage moving means, and the signal detection position, relative to the inspected wafer (inspected sample 9). FIG. 5A is an entire schematic view of the inspection wafer (inspected sample 9). In FIG. 5A, an arrow indicates the moving direction (Y-direction) of the stage moved by the stage moving means. FIG. 5B is an enlarged schematic view of a chip A. FIG. 5C is an enlarged schematic view of a cell B. In FIG. 5C, a mark of "O" indicates the signal detection position. The signal is detected in synchronization with both the charged particle beam scanning performed by the scanning means and the movement of the stage moving means. As shown in FIG. 5C, the scanning of the scanning means is performed in the X-direction, and the stage moving means controls positioning of the inspection wafer in turn in the Y-direction such that the inspection wafer is scanned in the order of lines (1), (2), (3), and . . . . Usually, when the inspection is performed while the pixel size is set to A nm, the inspection is performed while the signal is detected in A-nm pixel size (signal detection interval) in both the scanning direction and stage moving direction. Therefore, in cases where the pixel size is reduced according to the finer circuit pattern, for example, the pixel size is reduced to a half (A/2 nm), the number of signal detection positions becomes fourfold to remarkably degrade the throughput.

Figure 6A:
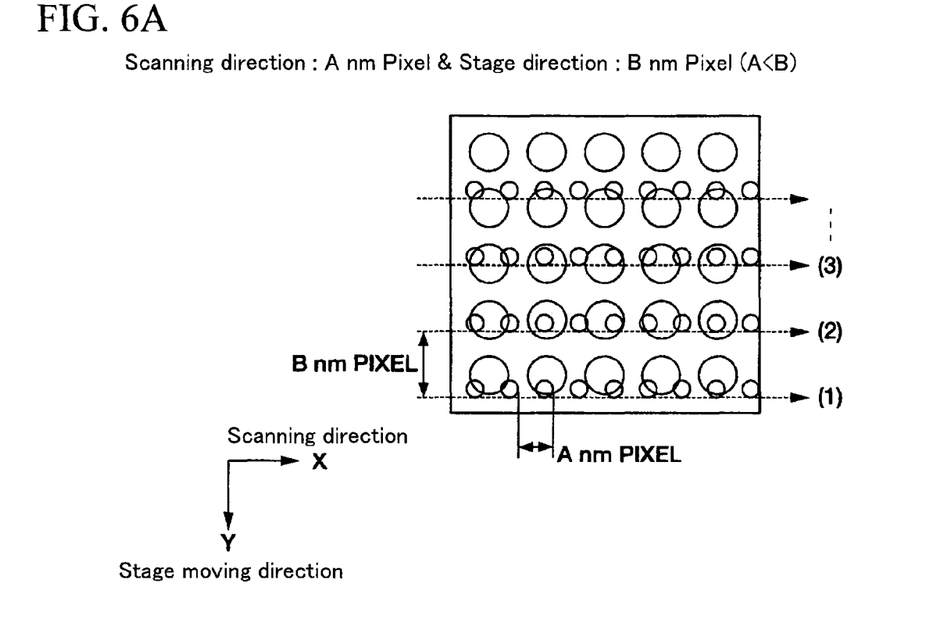
FIGS. 6A and 6B show a signal obtaining position when a pixel size in a scanning direction and a pixel size in a stage moving direction are set to different pixel sizes.
Figure 6B:
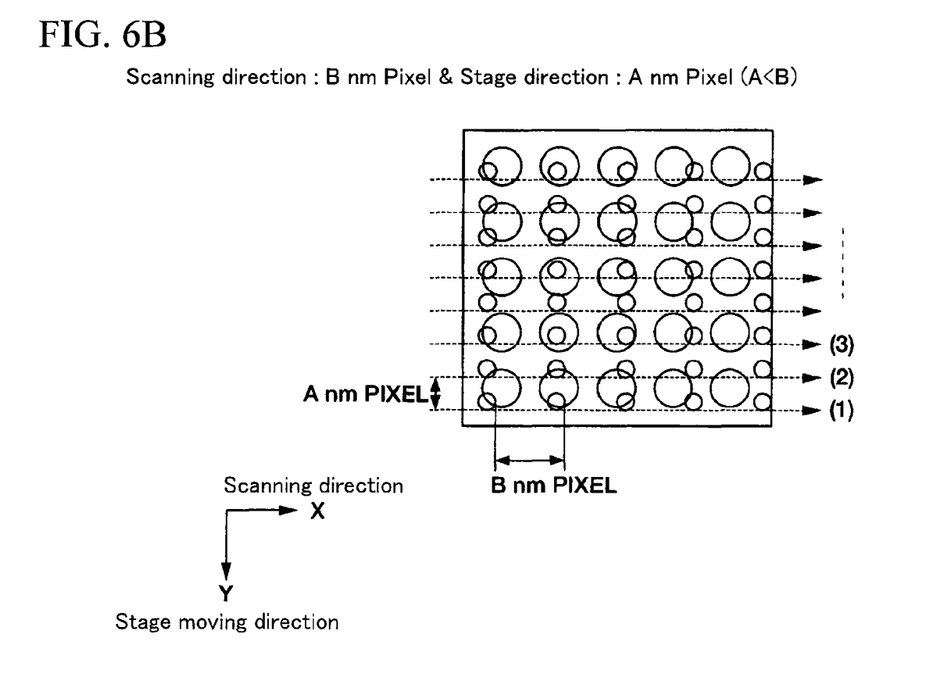

Therefore, in the invention, the pixel size in the scanning direction and the pixel size in the stage moving direction can separately be set. FIGS. 6A and 6B show the signal detection position when the different pixel sizes are set in the scanning direction and the stage moving direction. That is, FIG. 6A shows the signal detection position when the inspection is performed with the pixel size of A nm in the scanning direction and the pixel size of B nm (A<B) in the stage moving direction. FIG. 6B shows the signal detection position when the inspection is performed with the pixel size of B nm in the scanning direction and the pixel size of A nm (A<B) in the stage moving direction. In FIG. 6A, the inspection throughput is improved B/A times, compared with the case in which the inspection is performed with the pixel size of A nm in the stage moving direction. Similarly, in FIG. 6B, the inspection throughput is improved B/A times, compared with the case in which the inspection is performed with the pixel size of A nm in the scanning direction (in the case of the same scanning width). Thus, the inspection is performed while the pixel size is reduced only for the direction in which high resolution is required, so that the degradation in throughput can be prevented.

Figure 7:
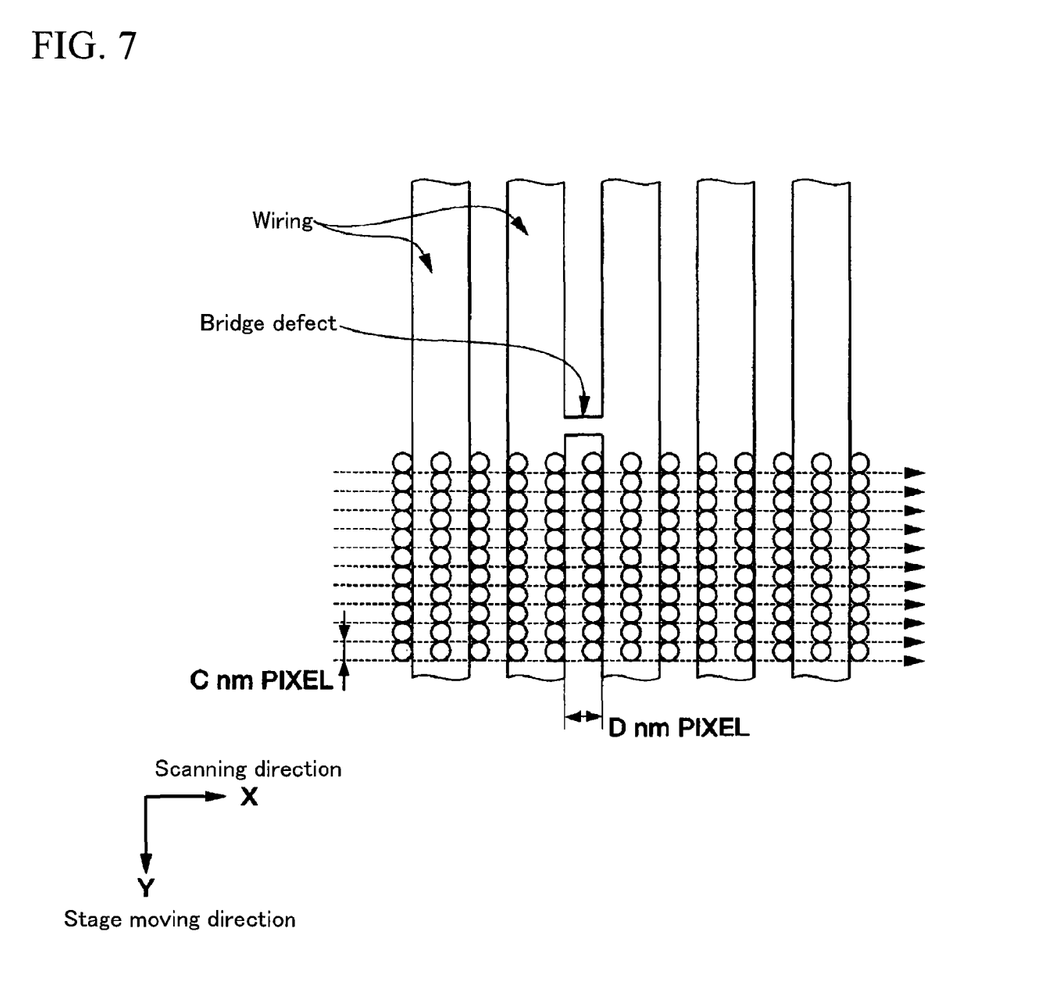
FIG. 7 shows signal obtaining positions in the scanning direction and the stage moving direction when a micro bridge defect formed between wiring patterns is detected.

FIG. 7 is a view explaining the pixel size adjustment in the scanning direction and the stage moving direction in the case of detecting a micro bridge defect formed between wiring patterns. As shown in FIG. 7, the micro bridge defect formed between wiring patterns is a defect which is long in the direction orthogonal to the wiring and extremely thin in the direction parallel to the wiring. While the pixel size is set to C run to enhance the accuracy in the stage moving direction parallel to the wiring, the pixel size is set to D nm (C<D) in the direction orthogonal to the wiring, and the inspection is performed. Therefore, the oversight of the thin defect in the direction orthogonal to the wiring (orthogonal to the stage moving direction), and the decrease in detection sensitivity can be prevented. At the same time, the improvement of throughput can be achieved because a certain large level of pixel size can be set in the scanning direction. Thus, because the fine defect in the wiring pattern is mainly formed in the direction orthogonal to the wiring, the inspection is effectively performed while the different pixel sizes are set in the X-direction and the Y-direction.

Figure 8A:
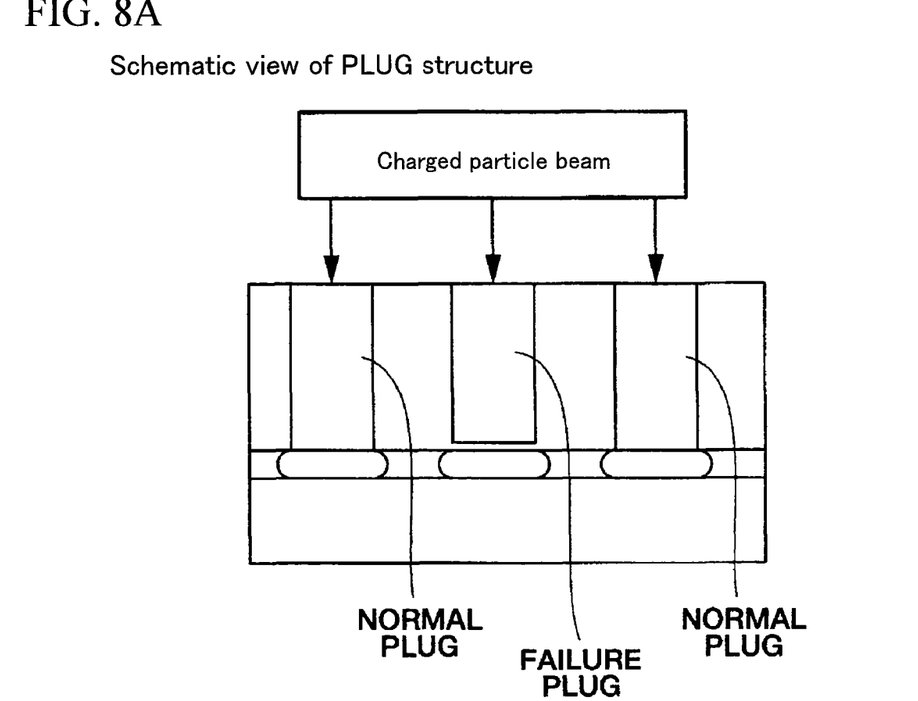
FIG. 8A is a schematic view showing plug structures of a normal plug and a failure plug.
Figure 8B:
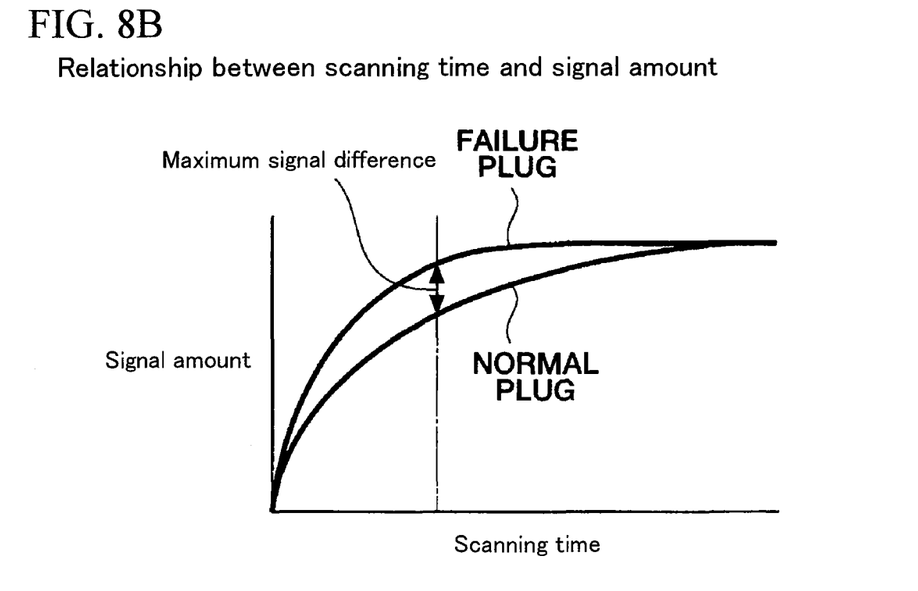
FIG. 8B shows a relationship between a scanning time and a signal amount for the normal plug and the failure plug.

FIG. 8A is a schematic view showing plug structures of a normal plug and a failure plug. When the normal plug and the failure plug are irradiated with the charged particle beam, the secondary electron generated by the irradiation, that is, the signal amount depends on the defect structure or the material. Generally a relationship between a scanning time and a signal amount for each of the normal plug and the failure plug is shown in FIG. 8B. As used herein, the scanning time shall mean a time to perform the next scan since the scan is performed. As shown in FIG. 8B, it is necessary to appropriately set the scanning time in order that a difference in signal amount between the normal plug and the failure plug becomes the maximum (, that is, the defect is clearly identified). That is, the defect detection sensitivity can be improved by selecting the scanning time according to the structure and material of the inspected sample.

Figure 9A:
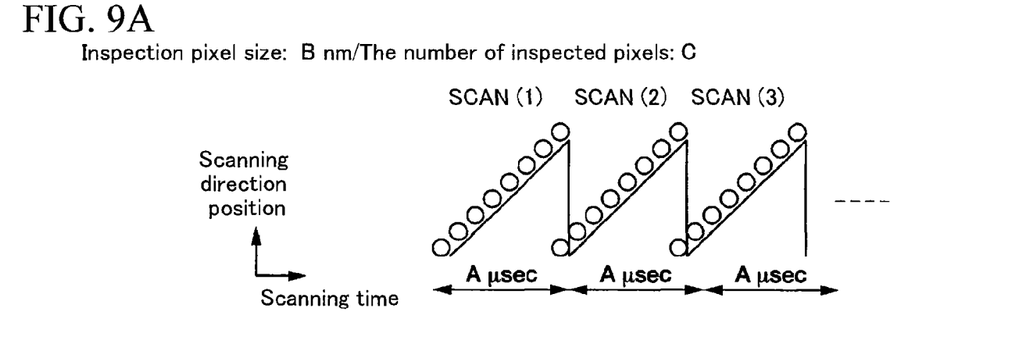
FIGS. 9A-9D are views explaining a relationship of both a scanning time and a scanning width to both an inspected pixel size and the number of inspected pixels.
Figure 9B:
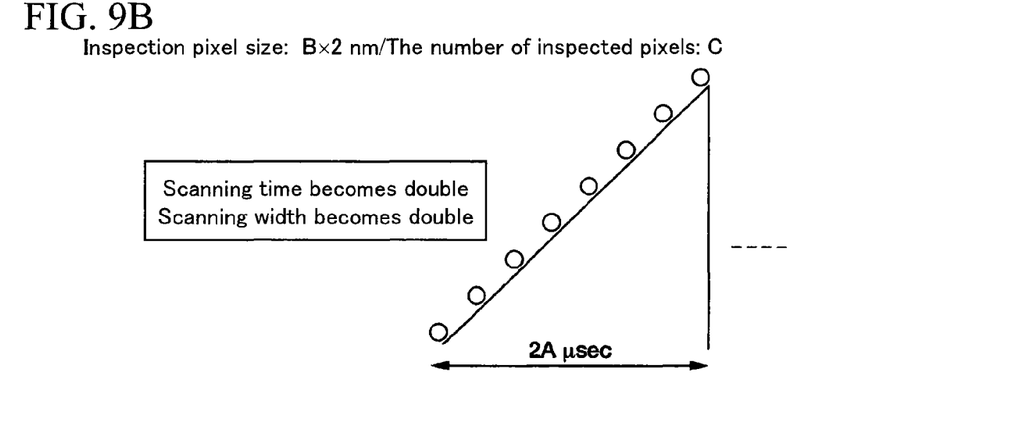
Figure 9C:
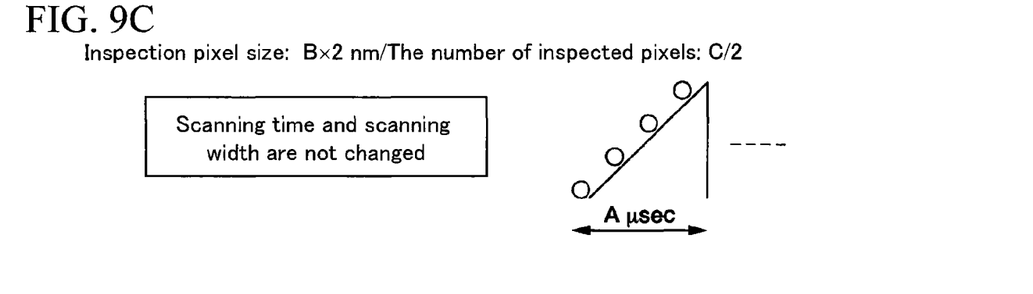
Figure 9D:
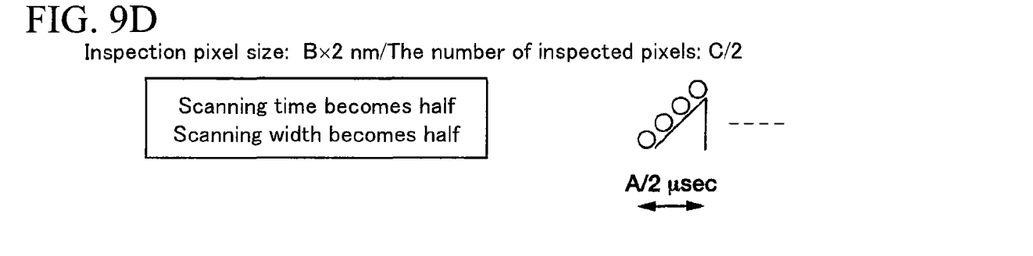

The scanning time can be changed by adjusting the inspected pixel size and the number of pixels as described below. FIGS. 9A-9D are views explaining a relationship of the scanning time and scanning width to the inspected pixel size and the number of inspected pixels. Assuming that B nm is the inspected pixel size and C is the number of inspected pixels, the relationship between the scanning time and the scanning width is defined as shown in FIG. 9A. At this point, when the number of inspected pixels and the inspected pixel size are changed, the results shown in FIGS. 9B to 9D are obtained. FIG. 9B shows the case in which the inspected pixel size becomes double (B×2 nm) while the number of inspected pixels is not changed (the number of pixels C). In FIG. 9B, both the scanning time and the scanning width become double. FIG. 9C shows the case in which the inspected pixel size becomes double (B×2 nm) while the number of inspected pixels becomes a half (the number of pixels C/2). In FIG. 9C, both the scanning time and the scanning width are not changed. FIG. 9D shows the case in which the inspected pixel size is not changed (B nm) while the number of inspected pixels becomes a half (the number of pixels C/2). In FIG. 9D, both the scanning time and the scanning width become a half. Thus, the scanning time can be adjusted by changing the inspected pixel size and the number of pixels. Therefore, the defect detection sensitivity can be improved by adjusting the inspected pixel size and the number of pixels according to the structure and material of the inspected sample. In the description of FIGS. 9A to 9D, it is assumed that the scanning speed of the scanning means is kept constant. However, the scanning time can also be adjusted by changing the scanning speed of the scanning means.

Thus, according to the invention, the inspected sample can be inspected with the different pixel sizes in the scanning direction and stage moving direction according to the structure of the circuit pattern of the inspected sample or the structure and material of the inspected sample, and the circuit pattern inspection method and circuit pattern inspection apparatus in which the degradation in inspection throughput is prevented can be provided.

DESCRIPTION OF REFERENCE NUMERALS 1 circuit pattern inspection apparatus
2 inspection chamber
3 electron optical system
4 optical microscope unit
5 image processor
6 input unit
7 secondary electron detecting unit
8 sample chamber
9 inspected sample
10 electron gun
11 electron beam extracting electrode
12 condenser lens
13 blanking deflector
14 aperture
15 scanning deflector
16 objective lens
17 beam reflector
18 ExB deflector
20 secondary electron detector
21 preamplifier
22 AD converter
23 light conversion means
24 light transmission means
25 electric conversion means
26 high-voltage power supply
27 preamplifier driving power supply
28 AD converter driving power supply
29 reverse bias power supply
30 sample stage
31 X-stage
32 Y-stage
33 rotary stage
34 position measuring and position controlling device
35 height measuring device
40 light source
41 optical lens
42 CCD camera
43 scanning signal generator
44 lens power supply
45 memory unit
46 comparison unit
47 determination unit
49 entire control unit
55 map display unit
56 image display unit
57 image obtaining instruction
58 image processing instruction
59 processing condition setting
60 mode switching
61 correction control circuit

What is claimed is:
1. A circuit pattern inspection apparatus comprising:
irradiation means for irradiating a sample with a charged particle beam, a circuit pattern being formed in the sample;
scanning means for scanning the sample with the charged particle beam in an X-direction;
stage moving means for moving a stage, on which the sample is placed, in a Y-direction, the Y-direction being different from the X-direction;
detection means for detecting a signal, the signal being generated from the sample by the irradiation with the charged particle beam;
memory means for storing an image of the circuit pattern in the sample, the image being obtained from the signal detected by the detection means;
comparison means for comparing the image stored in the memory means with an image obtained from another circuit pattern corresponding to the circuit pattern in the sample;
determination means for determining a defect on the circuit pattern from the comparison result performed by the comparison means; and
setting means for setting each of a pixel size in the X-direction and a pixel size in the Y-direction separately from, and independently of, each other, when the sample is moved in the Y-direction by the stage moving means and is scanned in the X-direction by the scanning means, the pixel size in the X-direction corresponding to the signal detection interval in the X-direction on the sample, the pixel size in the Y-direction corresponding to the signal detection interval in the Y-direction on the sample.
2. The circuit pattern inspection apparatus according to claim 1, wherein the setting means includes means for setting the number of pixels in the X-direction inspected by the scanning of the scanning means.

3. A circuit pattern inspection method comprising:

irradiating a sample in which a circuit pattern is formed with a charged particle beam to scan the sample in an X-direction for generating a signal from the sample, imaging the signal to obtain an image of the circuit pattern in the sample, comparing the image with an image obtained from another circuit pattern corresponding to the circuit pattern in the sample, and determining a defect on the circuit pattern is made based on the comparison result, wherein:

a pixel size in the X-direction and a pixel size in the Y-direction are set separately from, and independently of, each other, the Y-direction being different from the X-direction, when the sample is moved in the Y-direction and is scanned in the X-direction, the pixel size in the X-direction corresponds to the signal detection interval in the X-direction on the sample, and the pixel size in the Y-direction corresponds to the signal detection interval in the Y-direction on the sample.

4. The circuit pattern inspection method according to claim 3, further comprising performing inspection by setting each of the pixel size in the X-direction and the pixel size in the Y-direction to an arbitrary pixel size according to a structure of the circuit pattern or the structure and a material of the circuit pattern.

5. The circuit pattern inspection method according to claim 4, further comprising performing inspection by setting the number of pixels in the X-direction.

6. The circuit pattern inspection apparatus according to claim 1, wherein an inspection is performed by setting each of the pixel size in the X-direction and the pixel size in the Y-direction to an arbitrary pixel size according to a structure of the circuit pattern or the structure and a material of the circuit pattern.

* * * * *